United States Patent [19]

Hill et al.

[11] Patent Number: 4,488,973

[45] Date of Patent: Dec. 18, 1984

[54] PROCESS FOR AUGMENTING OR ENHANCING THE FRESH AIR AROMA OF CONSUMABLE MATERIALS AND CLOTHING AND COMPOSITION USEFUL FOR SAME

[75] Inventors: Ira D. Hill, Locust; Robert W. Trenkle, Bricktown; Braja D. Mookherjee, Holmdel; Robin K. Wolff, Point Pleasant, all of N.J.

[73] Assignee: International Flavors & Fragrances Inc., New York, N.Y.

[21] Appl. No.: 597,412

[22] Filed: Apr. 6, 1984

Related U.S. Application Data

[62] Division of Ser. No. 535,795, Sep. 26, 1983, , which is a division of Ser. No. 384,959, Jun. 4, 1982, Pat. No. 4,434,086.

[51] Int. Cl.[3] .................... D06M 13/12; D06M 13/02; A61K 7/035

[52] U.S. Cl. ................................ 252/8.6; 252/174.11; 424/69

[58] Field of Search ............................ 252/8.6, 174.11; 424/69

[56] References Cited

PUBLICATIONS

Technical Bulletin, No. 24, Applied Science Div., Milton Roy Co. Lab. Gp., TENAX-GC®.

Supran, "Lipids as a Source of Flavor", ACS, Symposium Series 75, (1978).

Bailey, "Cottonseed & Cottonseed Products", (1948), pp. 374–375.

Schultz, et al., "Symposium on Foods", (1962), pp. 220–229.

Arctander, "Perfume & Flavor Chemicals", vol. II, (1969), 2343, 2397, 3028, 2984; vol. I, 1105, 1106, 1494 and 1495.

*Primary Examiner*—Maria Parrish

*Attorney, Agent, or Firm*—Arthur L. Liberman

[57] ABSTRACT

Described is a process for imparting an "air dried cloth" aroma to cloth, synthetic or natural, previously dried using a clothes drier, comprising the step of contacting the cloth prior to drying with an aroma augmenting or enhancing quantity of either (i) a mixture consisting essentially of:

(a) from about 0.5 up to about 5% by weight of said composition of n-hexanal;

(b) from about 2 up to about 12% by weight of said composition of n-heptanal;

(c) from about 5 up to about 15% by weight of said composition of n-octanal;

(d) from about 40 up to about 70% by weight of said composition of n-nonanal;

(e) from about 10 up to about 30% by weight of said composition of n-decanal;

(f) from about 0.5 up to about 5% by weight of said composition of n-undecanal;

(g) from about 0.5 up to about 5% by weight of said composition of n-dodecanal;

(h) from about 0.5 up to about 5% by weight of said composition of n-tridecanal;

(i) from about 0 up to about 5% by weight of said composition of n-tetradecanal;

(j) from about 0 up to about 5% by weight of said composition of n-pentadecanal;

or (ii) first contacting the cloth with at least one organic acid selected from the group consisting of oleic acid, linoleic acid, and linolenic acid or a glyceride ester thereof, then exposing the resultant treated cloth to air and light in the ultra violet wavelengths prior to drying.

5 Claims, 15 Drawing Figures

GLC PROFILE FOR EXAMPLE I(A)

GLC PROFILE FOR EXAMPLE I(B)

GLC PROFILE FOR EXAMPLE II.

GLC PROFILE FOR EXAMPLE II.

GLC PROFILE FOR EXAMPLE III (A)

GLC PROFILE FOR EXAMPLE III (B)

GLC PROFILE FOR EXAMPLE III(C)

GLC PROFILE FOR EXAMPLE III

FIG. 13
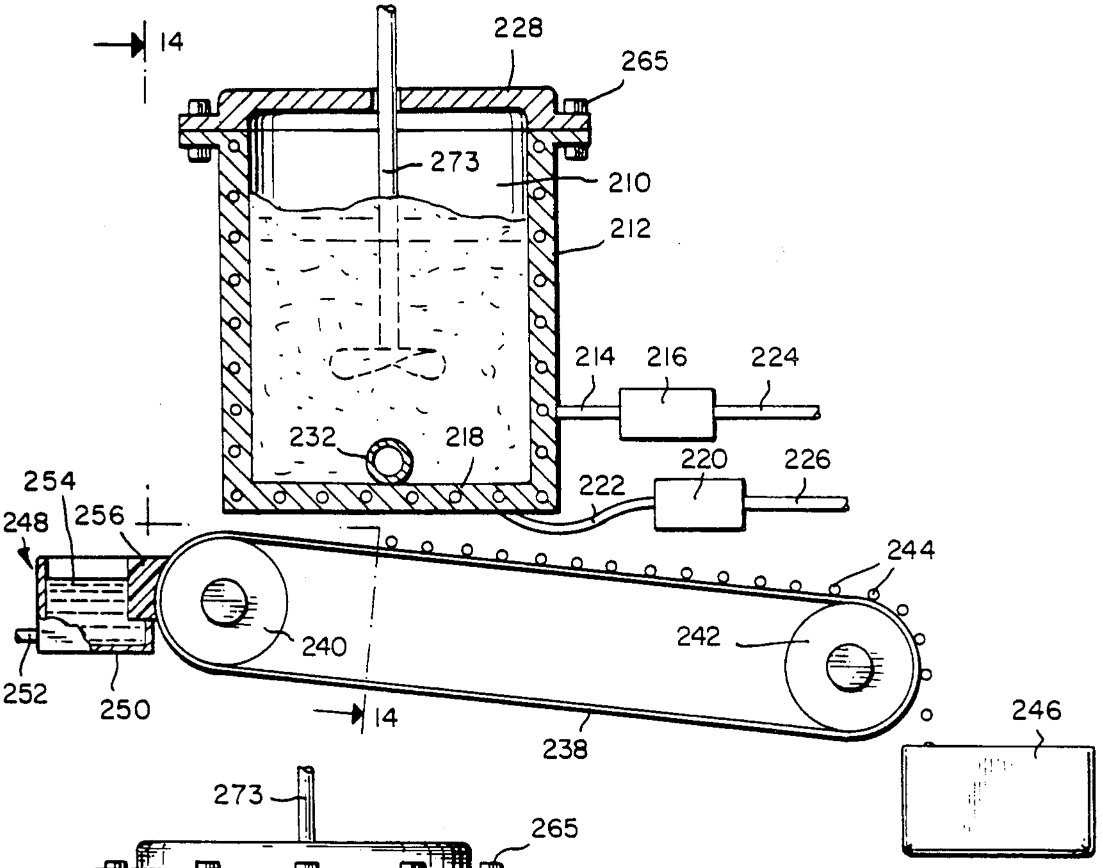
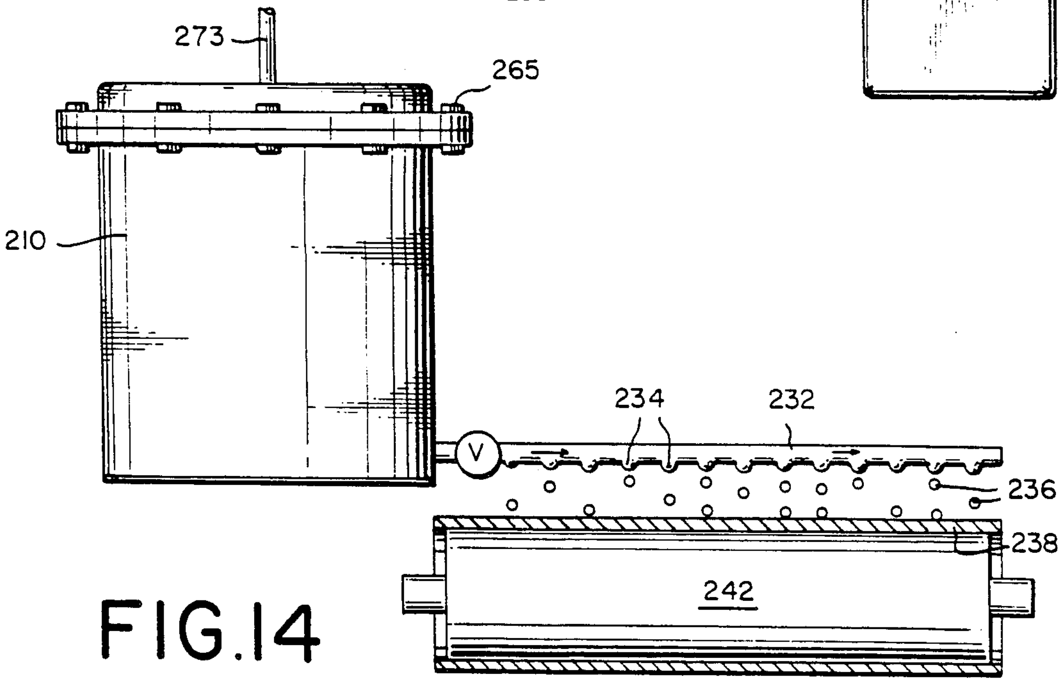
FIG. 14

PROCESS FOR AUGMENTING OR ENHANCING THE FRESH AIR AROMA OF CONSUMABLE MATERIALS AND CLOTHING AND COMPOSITION USEFUL FOR SAME

This is a divisional of application Ser. No. 535,795, filed Sept. 26, 1983 which is a stream-line divisional of U.S. Letters Patent, Ser. No. 384,959, filed on June 6, 1982, now U.S. Pat. No. 4,434,086, issued Feb. 28, 1983.

BACKGROUND OF THE INVENTION

With the advent of the use of automatic machinery to wash and dry clothing, particularly clothing fabricated from cotton, nylon and polyester fabrics, a need has been created for the imparting to clothing dried using an automatic clothing drier of a "fresh air aroma" of the type imparted to clothing dried by means of exposure to fresh air and natural light.

The prior art indicates that straight chain aldehydes are useful in augmenting or enhancing the aroma of perfume compositions, colognes and perfumed articles. Thus, Arctander "Perfume and Flavor Chemicals (Aroma Chemicals)", published by the author in 1969 discloses that n-nonanal is useful in augmenting or enhancing or imparting floral aromas at monograph 2343. By the same token, Arctander indicates that n-octanal is useful in imparting citrusy and floral aromas at monograph 2397. n-undecanal is shown at monograph 3028 of Arctander to be useful in imparting "fresh air" odors and also to have a floral and refreshing odor.

By themselves, however, the straight chain alkanals do not create the full "natural" fresh air aroma so necessary to impart a "natural effect" to dried clothing.

We discovered the constituents of "air dried" aroma by putting washed cotton cloth through a standard washing cycle and then air drying same in the presence of sunlight and then analyzing the head space above the fresh air dried-natural light exposed cotton cloth for the primary constituents in the "fresh air dried" aroma. We also determined that by means of imparting, prior to exposure to air and light, to cotton cloth, nylon cloth or polyester cloth an unsaturated organic acid, e.g. linolenic acid, linoleic acid or oleic acid or a glyceride ester thereof and then exposing same to light, a similar fresh air aroma is produced. Indeed, the said "fresh air" aroma to cloth is augmented by the combination of either (a) first adding to the cloth a mixture of straight chain aldehydes and then (b) adding to the cloth a mixture of or an individual organic unsaturated acid and finally, (c) exposing the resultant cloth to ultraviolet light and air; or (i) first treating the cloth with an unsaturated acid such as linolenic acid, linoleic acid or oleic acid; then (ii) exposing the cloth to ultraviolet light and air and (iii) adding to the cloth a mixture of unsaturated aldehydes to be specified infra.

The text, "Symposium on Foods: Lipids and Their Oxidation" Schultz, Day and Sinnhuber published by the Avi Publishing Company, 1962, discloses at page 220, 221 and 222 at Table 36 the production of volatile compounds including saturated $C_4$, $C_5$, $C_6$, $C_7$, $C_8$ and $C_9$ aldehydes from unsaturated fatty acids by means of natural autooxidation.

The text entitled "Cottonseed and Cottonseed Products, Their Chemistry and Chemical Technology" by Alton E. Bailey published by Interscience Publishers, Inc. of New York (1948) discloses the presence of unsaturated acids such as linolenic acid in cottonseed oil.

In addition, chemical compositions which can provide air and sunlight-dried cloth, fresh and linen-like, powerful and long-lasting aroma nuances are highly desirable in the art of perfumery. Many of the natural materials and processes which can be used to provide such fragrances and contribute such desired nuances to perfumery compositions are high in cost, unobtainable at times, vary in quality from one batch to another and/or are generally subject to the usual variations of natural products and results of natural processes.

There is, accordingly, a continuing effort to find synthetic materials which will replace, enhance or augment the essential fragrance notes provided by natural essential oils or compositions thereof. Unfortunately, many of these synthetic materials either have the desired nuances only to a relatively small degree or else contribute undesirable or unwanted odor to the composition. The search for materials which can provide a more refined, powerful, long-lasting, stable air and sunlight-dried cloth, fresh, linen-like aroma has been difficult and relatively costly in the areas of both natural products and synthetic products.

OBJECTS OF THE INVENTION

It is an object of our invention to provide a process for imparting a "fresh air aroma" to cloth during the washing-drying cycle.

It is another object of our invention to provide a composition of matter useful in carrying out the process of imparting a fresh air aroma to clothing subsequent to a washing-drying cycle.

It is another object of our invention to provide a "fresh air aroma" to cloth subsequent to the wash-dry cycle which cloth is either nylon, polyester or cotton.

It is a further object of our invention to provide a process for augmenting or enhancing powerful, long-lasting, air and sunlight-dried cloth, fresh, and linen-like aroma nuances to perfume compositions, perfumed articles and colognes in an effective, efficient and low-cost manner.

(a) treated with unsaturated organic acids; then
(b) treated with air and ultraviolet light; then
(c) treated with a mixture of straight chain saturated aldehydes;

prior to entering the drying cycle.

Figure 4B:
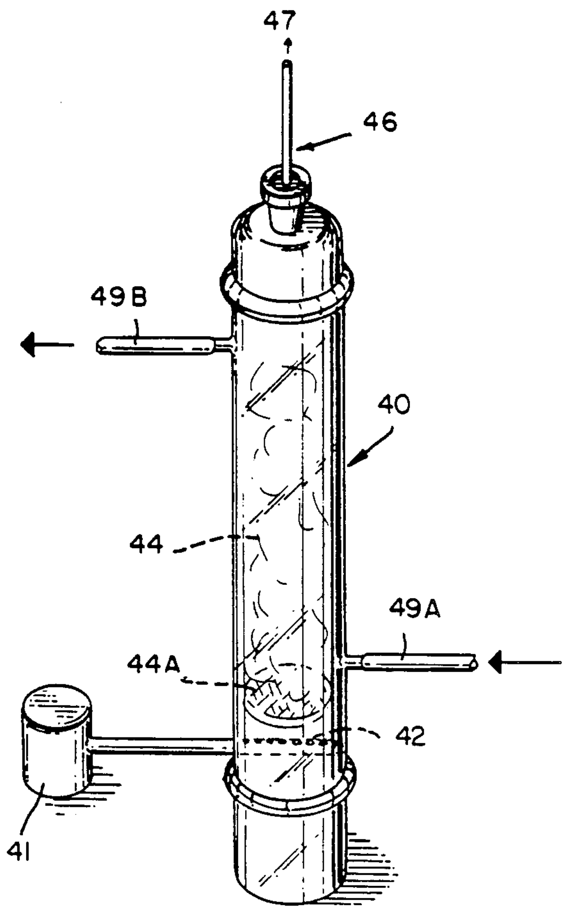
Figure 4A:
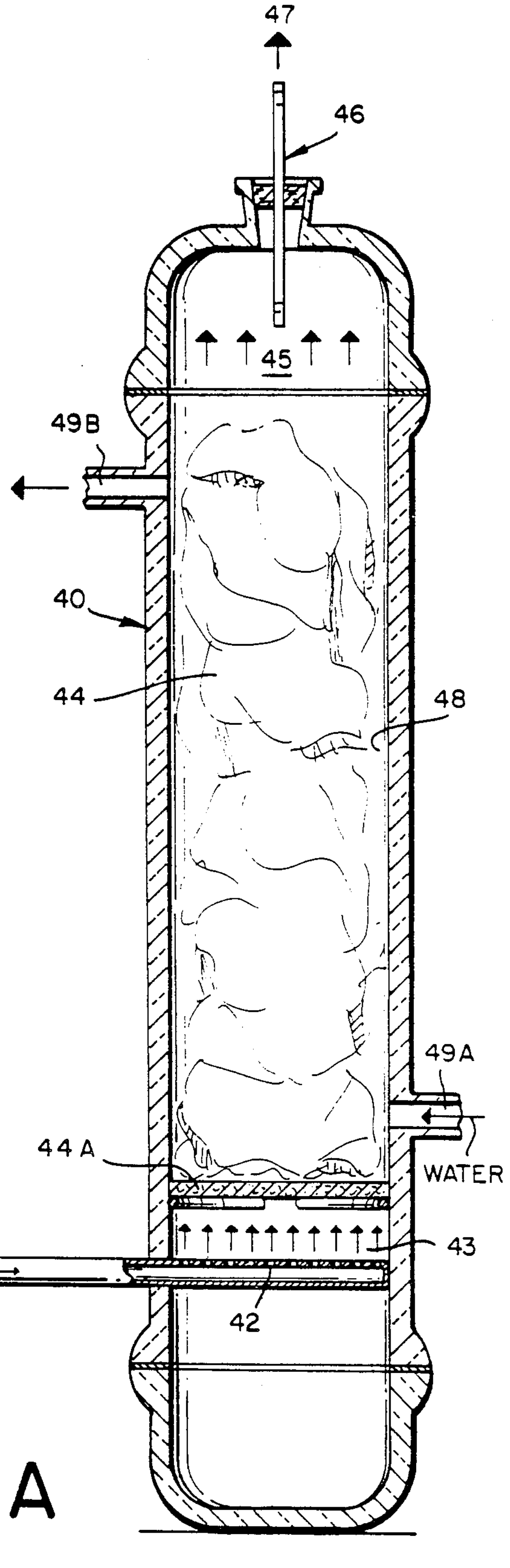
Figure 4A:
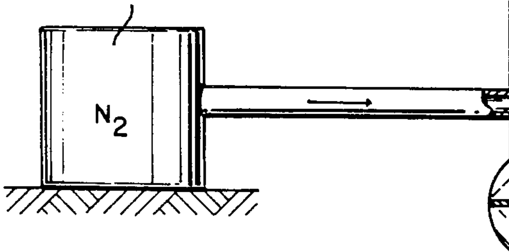

FIG. 4(A) is a side view cut-away diagram of apparatus used for trapping head space volatiles existing in such substances as cloth. Said head space volatile trapping apparatus is particularly useful in determining the components of the "fresh air aroma" imparted to cotton cloth as a result of fresh air/natural light drying subsequent to the normal wash cycle.

FIG. 4(B) is a perspective view of the head space volatile trapping apparatus of FIG. 4(A).

Figure 5:
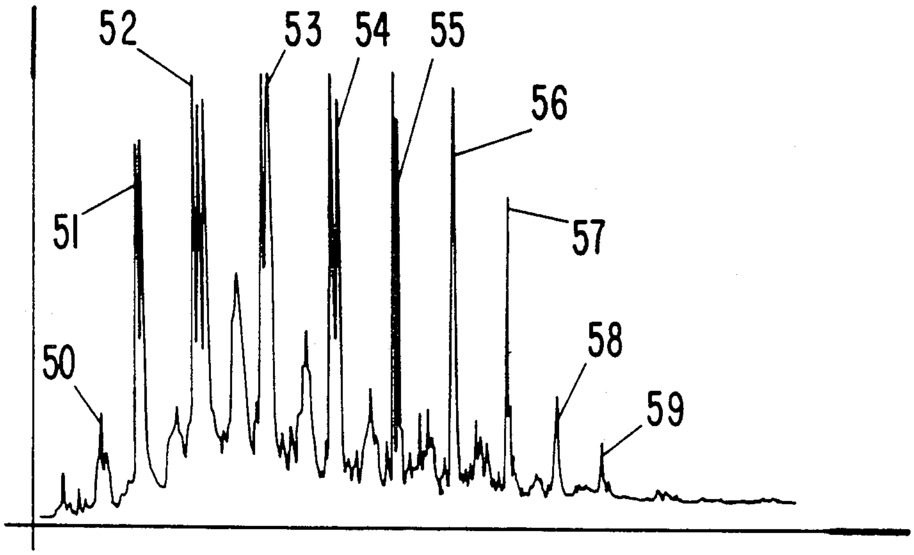

FIG. 5 is the GLC profile of the trapped head space volatiles produced according to Example I(A) (conditions: 400'×0.32" SE-30 column programmed at 70°-200° C. at 2° and 4° C. per minute).

Figure 6:
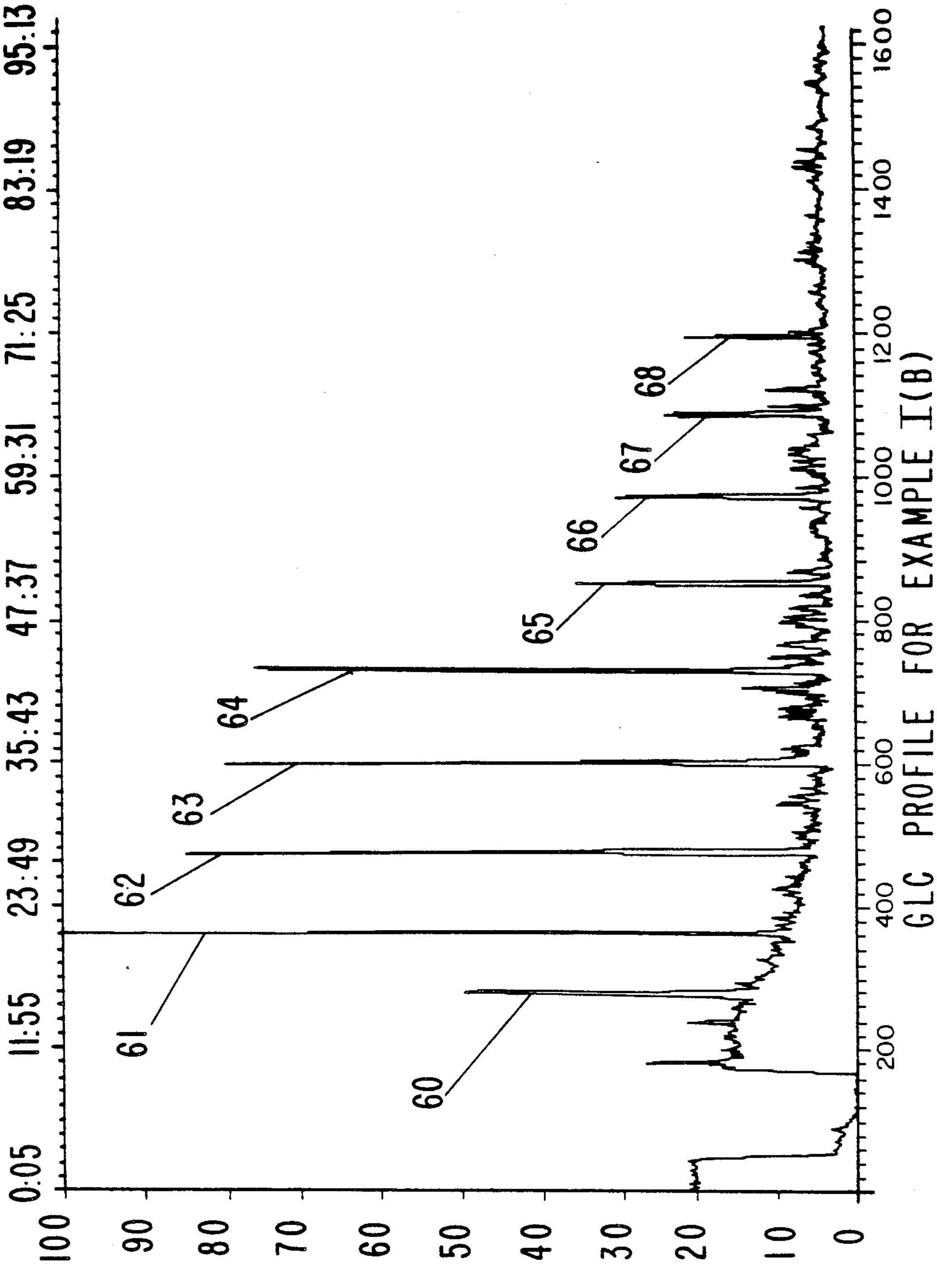

FIG. 6 is the GLC profile of the trapped head space volatiles produced according to Example I(B) from fresh air dried cotton cloth (conditions: 400'×0.32" SE-30 column programmed at 70°-200° C. at 2° and 4° C. per minute).

Figure 7:
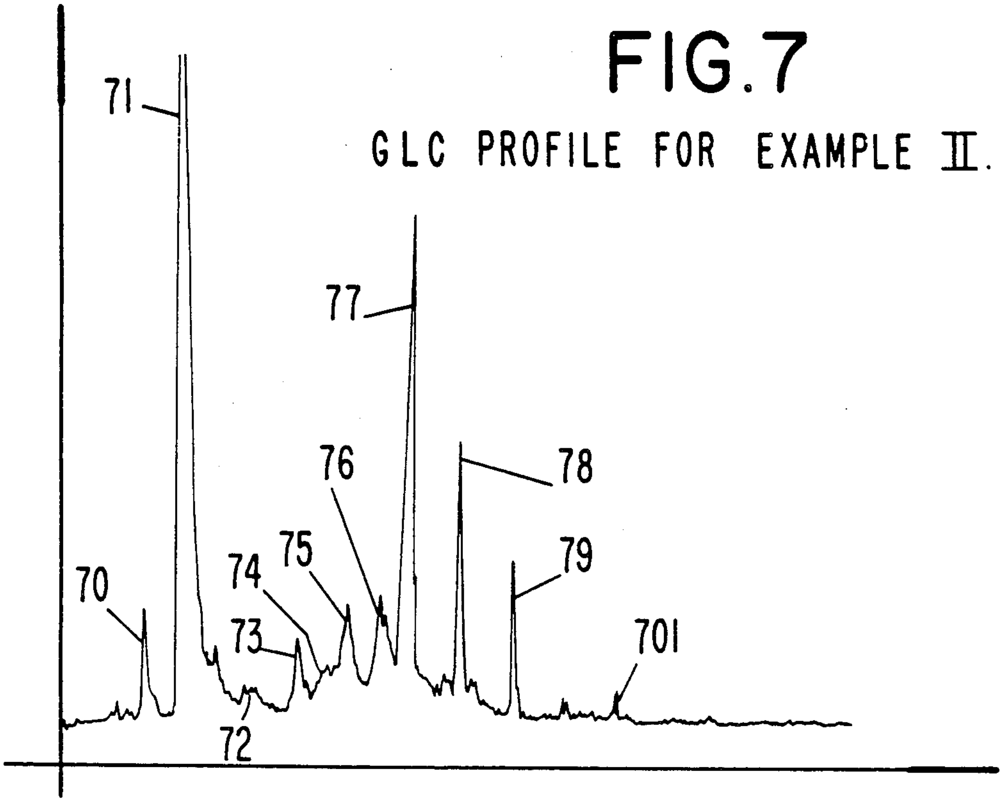

FIG. 7 is the GLC profile of the head space volatiles trapped from the head space over fresh air dried paper previously impregnated with cottonseed oil (conditions: 400'×0.32" SE-30 column programmed at 70°-200° C. at 2° and 4° C. per minute).

Figure 8:
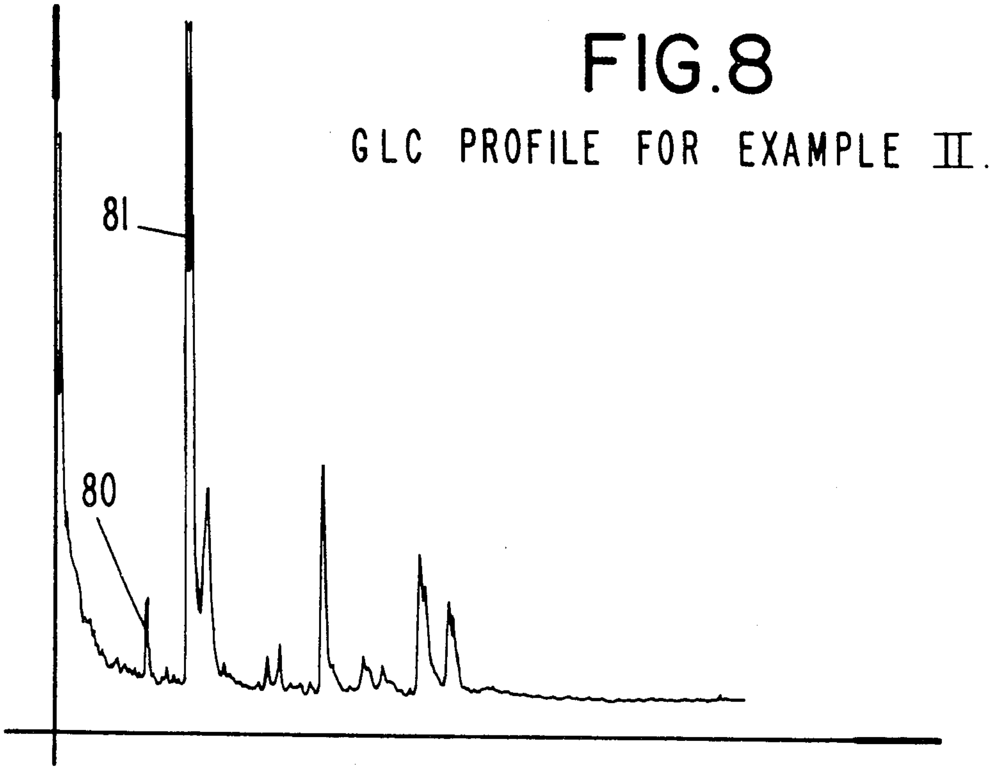

FIG. 8 is the GLC profile of the head space volatiles trapped according to the process of Example II using the apparatus of FIGS. 4(A) and 4(B) of paper previously impregnated with cottonseed oil dried using an automatic clothes drier (conditions: 400'×0.32" SE-30 column programmed at 70°-200° C. at 2° and 4° C. per minute).

Figure 9:
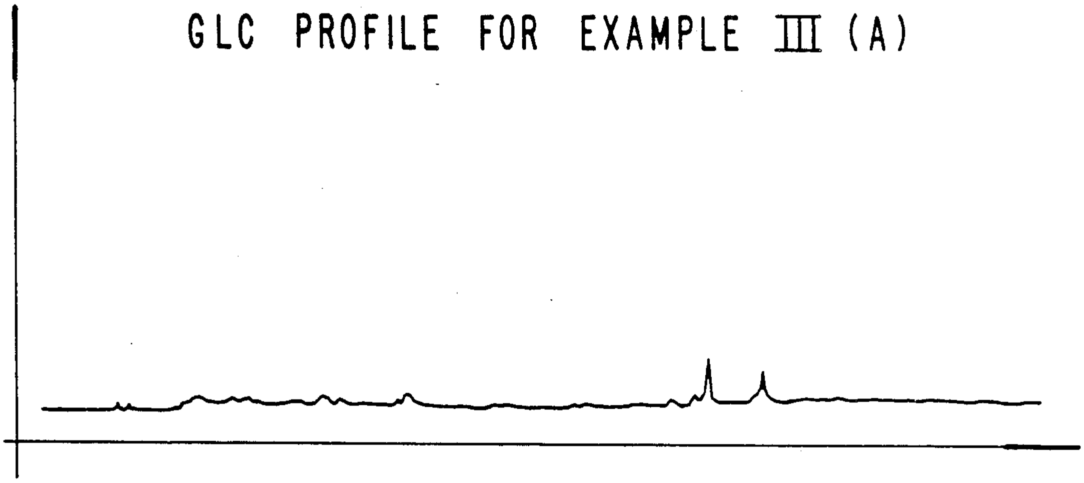

FIG. 9 is the GLC profile of the head space volatiles trapped from the head space over untreated filter paper using the apparatus of FIGS. 4(A) and 4(B) according to Example III(A) (conditions: 400'×0.32" SE-30 column programmed at 70°-200° C. at 2° and 4° C. per minute).

Figure 10:
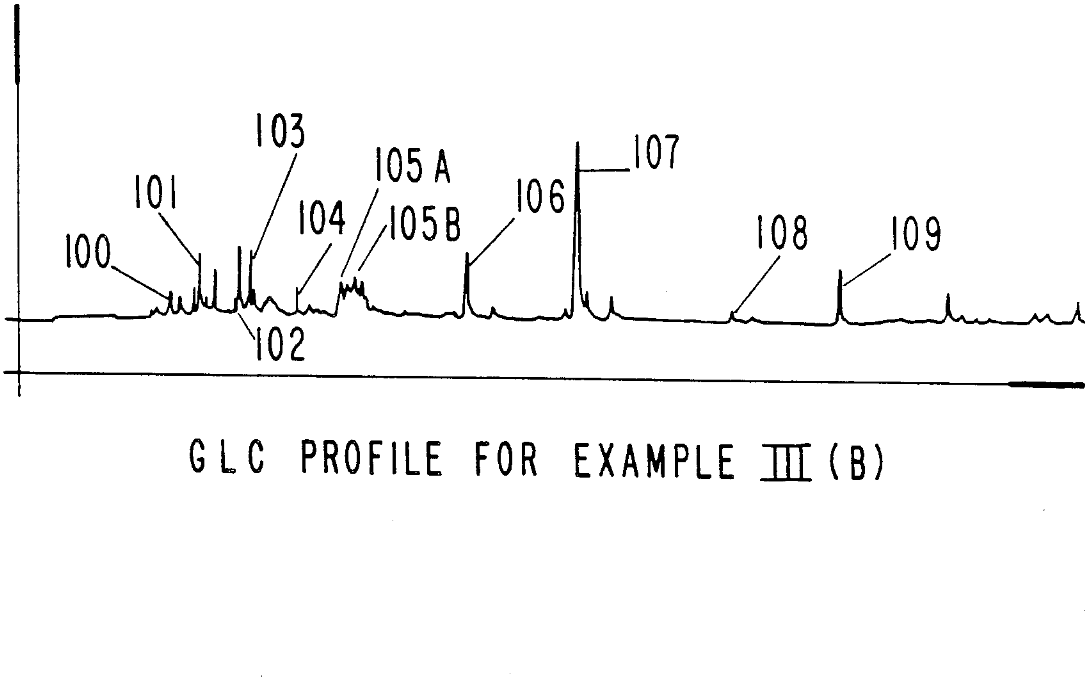

FIG. 10 is the GLC profile of the trapped head space volatiles over untreated polyester cloth using the apparatus of FIGS. 4(A) and 4(B). The head space volatiles are trapped using the procedure of Example III(B). Conditions: 400'×0.32" SE-30 column programmed at 70°-200° C. at 2° and 4° C. per minute.

Figure 11:
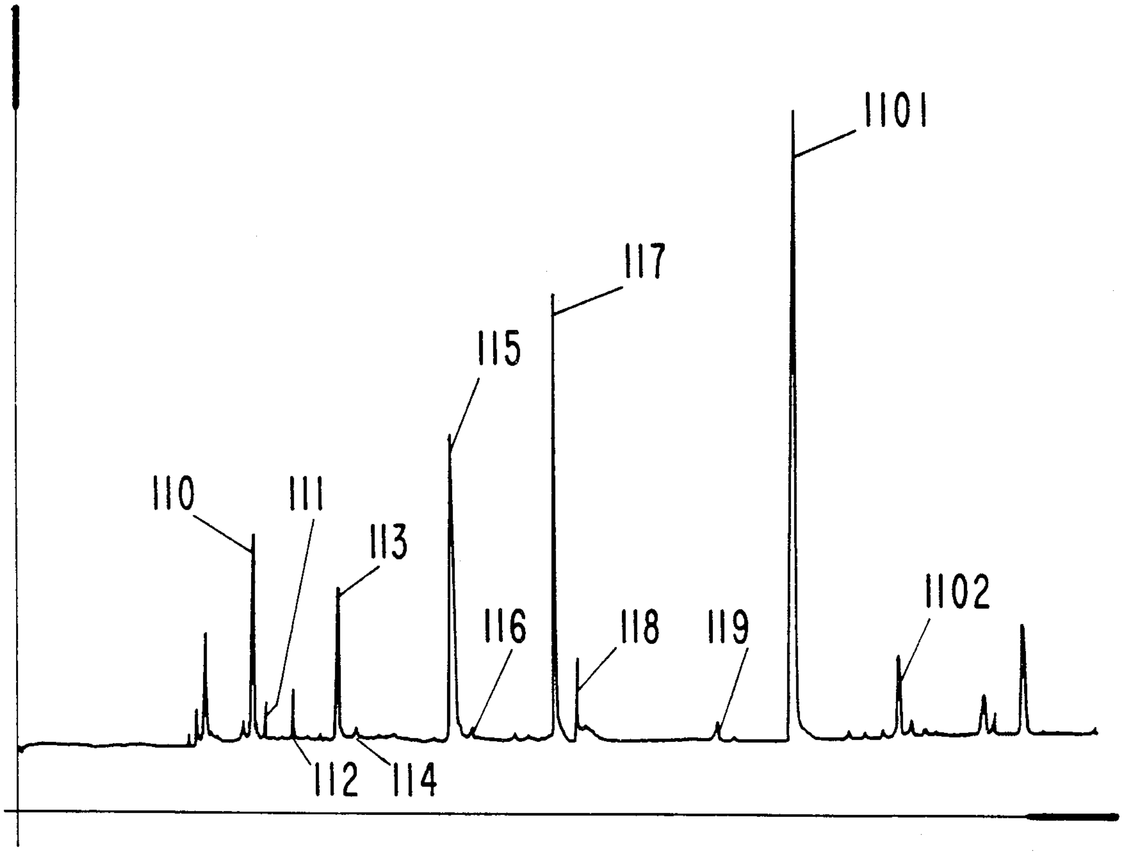

FIG. 11 is the GLC profile of trapped head space volatiles over nylon cloth using apparatus of FIGS. 4(A) and 4(B). The volatile head space trapping is carried out according to the procedure of Example III(C). The conditions of the GLC apparatus are: 400'×0.32" SE-30 column programmed at 70°-200° C. at 2° and 4° C. per minute.

Figure 12:
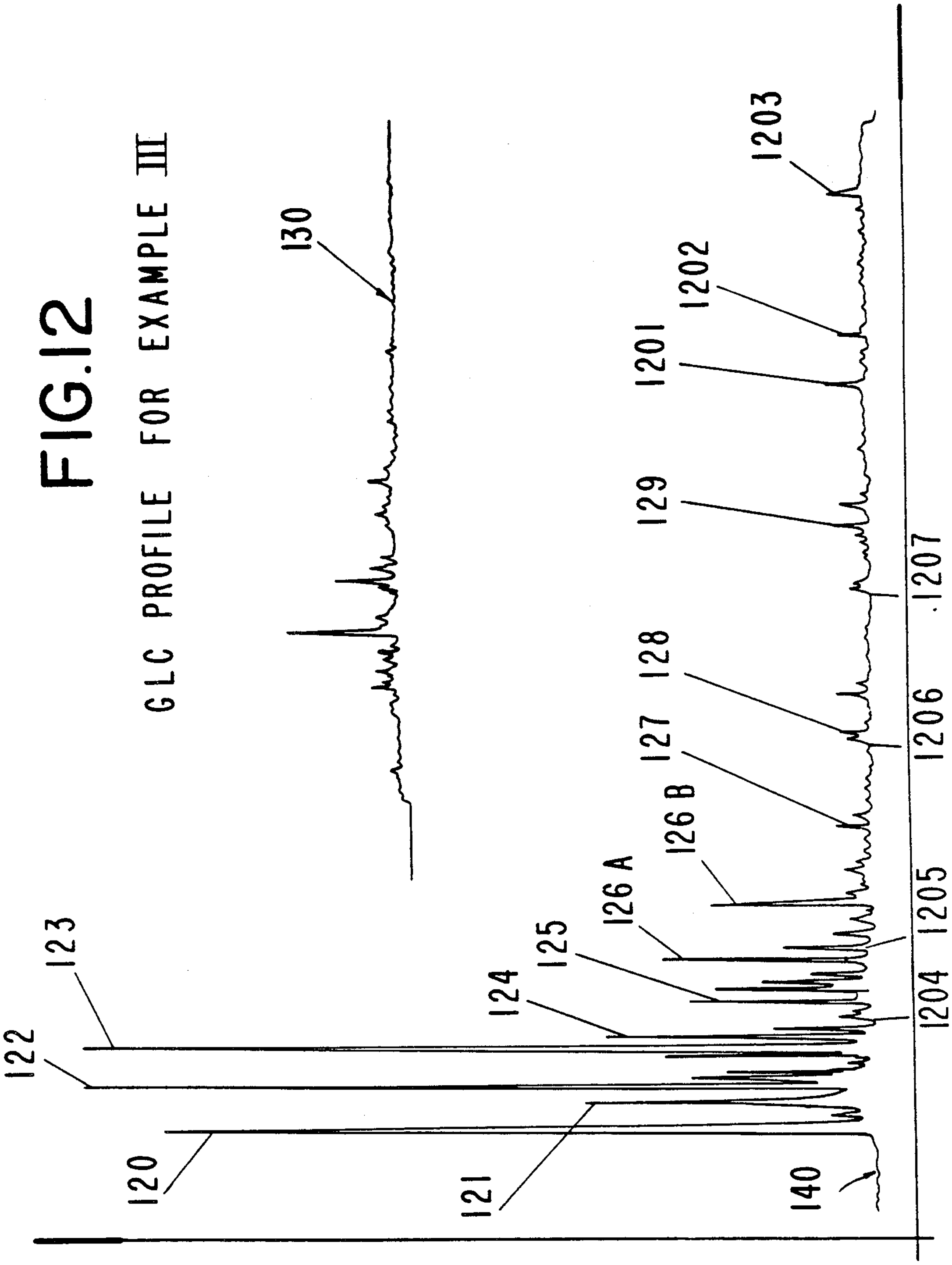

FIG. 12 is the GLC profile of the air used in extracting the volatiles from the cloth into the head space in each of Examples III(A), III(B) and III(C). The profile indicated by reference numeral "130" is an original GLC profile on an original air sample. The profile indicated by reference numeral "140" is the profile for the transferred concentrate of profile 130 onto Tenax-GC® polymer using a NuTech 221 AC/DC gas sampler manufactured by the NuTech Corporation of Durham, N.C.

FIG. 13 is a partial side elevation and partial sectional view of an apparatus for forming polyethylene pellets scented with the composition of our invention.

FIG. 14 is a section taken on the line 14—14 of FIG. 13.

DETAILED DESCRIPTION OF THE PREFERRED EMBODIMENTS OF THE INVENTION AND DETAILED DESCRIPTION OF THE DRAWINGS

Figure 1:
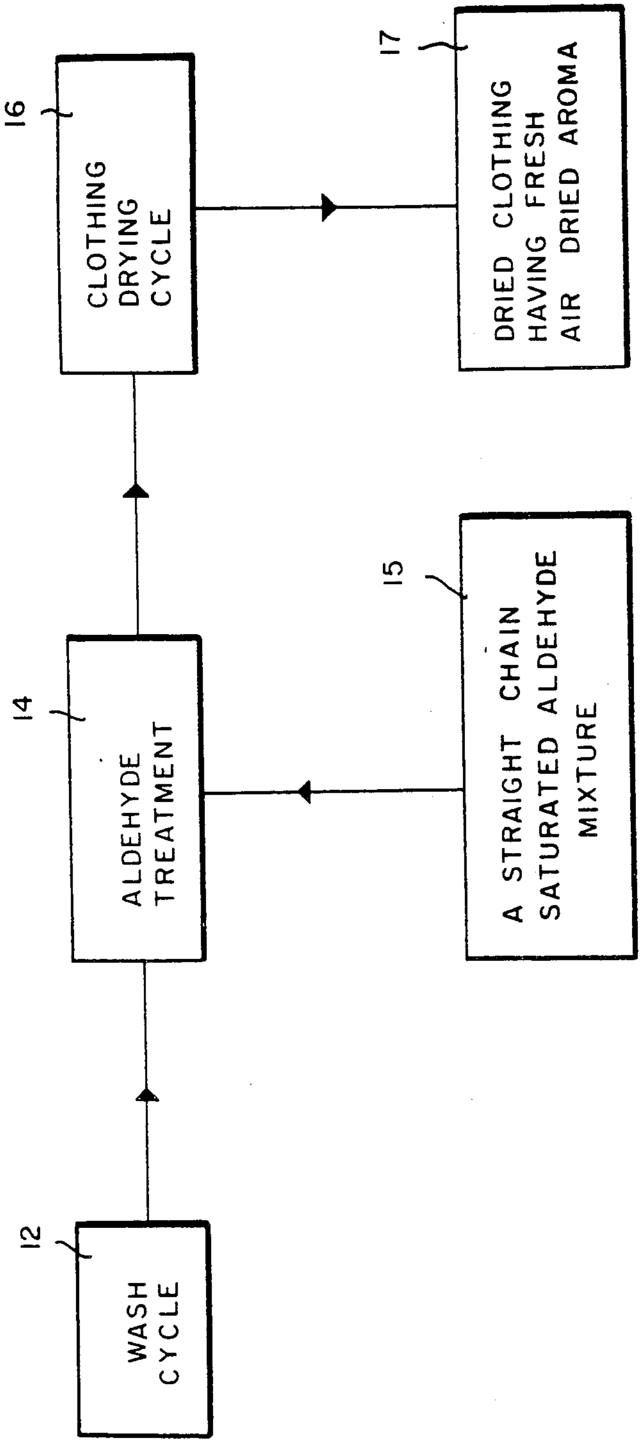
FIG. 1 is a schematic block flow diagram indicating the preferred method of treating cloth evolving from the wash cycle with a composition of matter consisting essentially of a straight chain saturated aldehyde mixture.

In accordance with a preferred embodiment as set forth in the block flow diagram of FIG. 1, cloth is washed in wash cycle 12 and then rinsed and treated with a straight chain saturated aldehyde mixture 15 at aldehyde treatment station 14 prior to drying cycle 16.

The straight chain aldehyde composition is preferably as follows:

(a) from about 0.5 up to about 5% by weight of said composition of n-hexanal;
(b) from about 2 up to about 12% by weight of said composition of n-heptanal;
(c) from about 5 up to about 15% by weight of said composition of n-octanal;
(d) from about 40 up to about 70% by weight of said composition of n-nonanal;
(e) from about 10 up to about 30% by weight of said composition of n-decanal;
(f) from about 0.5 up to about 5% by weight of said composition of n-undecanal;
(g) from about 0.5 up to about 5% by weight of said composition of n-dodecanal;
(h) from about 0.5 up to about 5% by weight of said composition of n-tridecanal;
(i) from about 0 up to about 5% by weight of said composition of n-tetradecanal;
(j) from about 0 up to about 5% by weight of said composition of n-pentadecanal.

The clothing evolving from drying cycle 16, which is carried out in the standard automatic clothes drier has a fresh air dried aroma at station 17.

Figure 2:
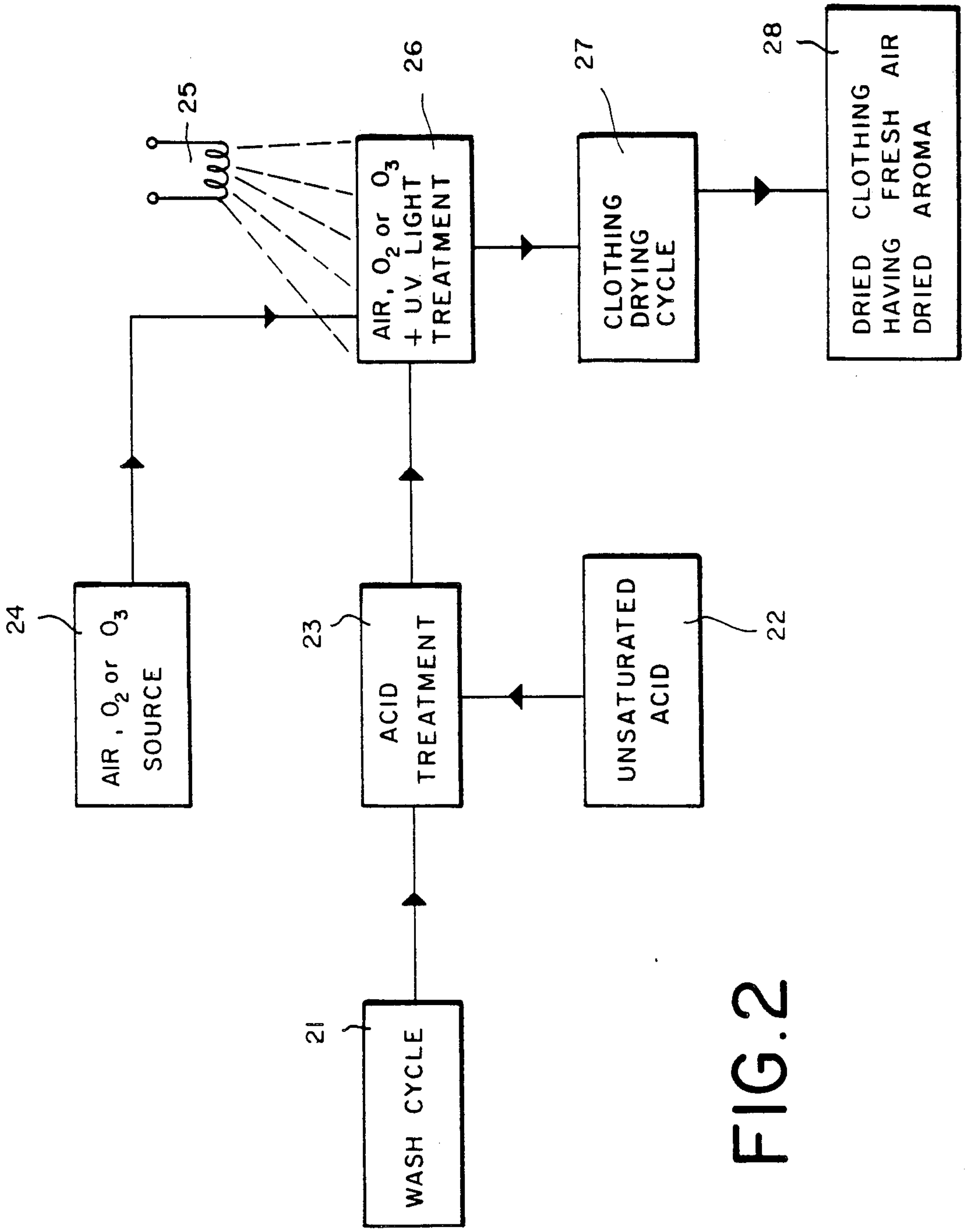
FIG. 2 is a block flow diagram setting forth a preferred embodiment of the process of our invention wherein unsaturated organic acids are used to treat cloth evolving from a wash cycle prior to air and ultraviolet light treatment of the acid-treated cloth.

In a second preferred embodiment of the process of our invention as set forth in the block flow diagram of FIG. 2, clothing treated in wash cycle 21 is treated with at least one organic acid selected from the group consisting of oleic acid, linoleic acid and linolenic acid or at least one glyceride ester thereof from unsaturated acid source 22 at station 23. The acid treated, rinsed clothes are then exposed to air, oxygen or ozone at a pressure of about 1 up to about 50 atmospheres and prior to, subsequent to or simultaneously therewith, also exposed to ultraviolet light rays from UV source 25 at station 26. The thus-treated clothing is then passed through a clothing drying cycle at station 27 (using an automatic clothes drier) and yields an enhanced fresh air dried aroma at station 28.

Figure 3:
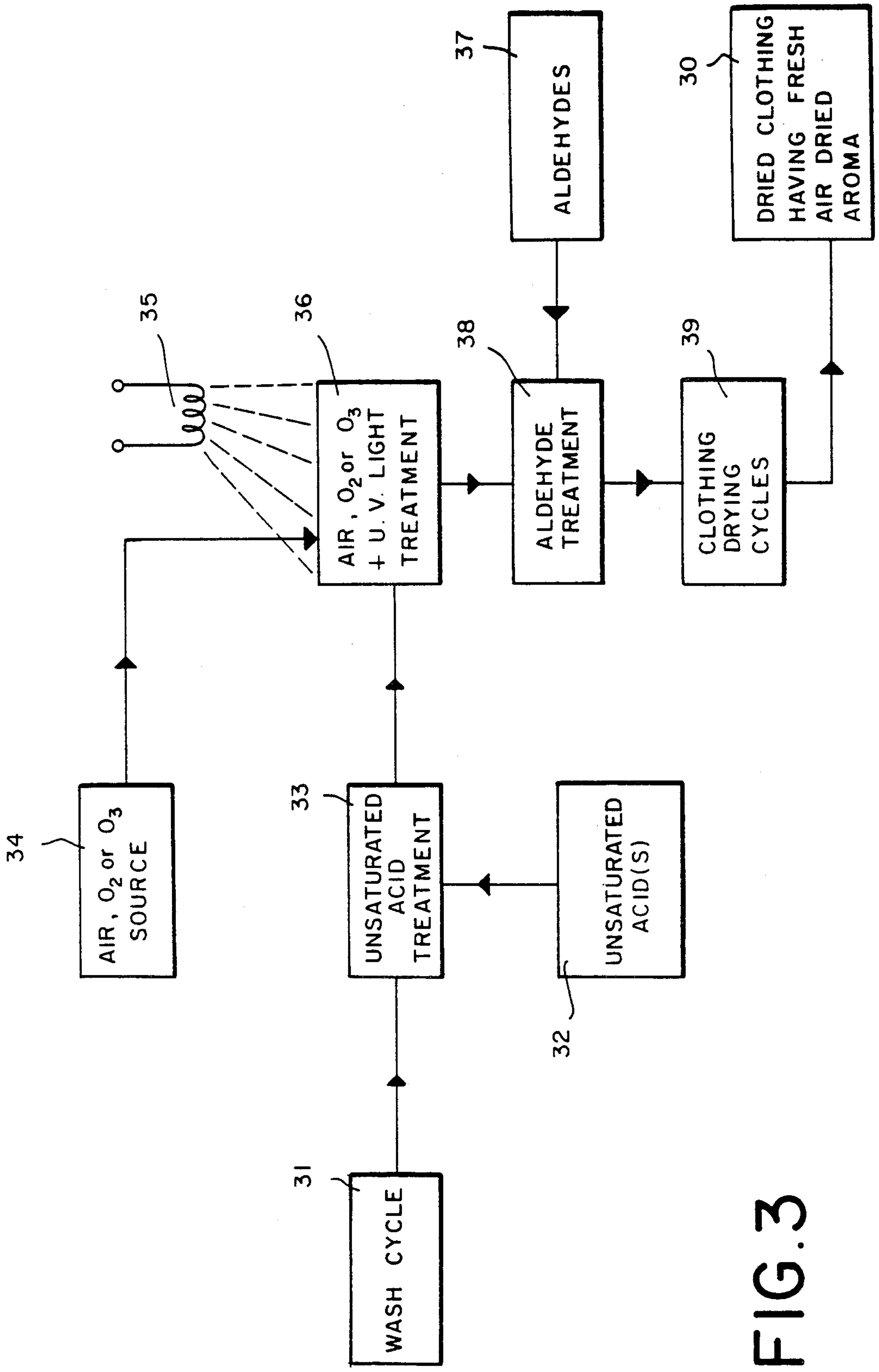
FIG. 3 is a block flow diagram setting forth a preferred embodiment of the process of our invention wherein cloth evolving from the wash cycle is.

FIG. 3 illustrates a block flow diagram of another preferred process of our invention. Rinsed clothes evolving from wash cycle 31 is treated with at least one unsaturated acid selected from the group consisting of oleic acid, linoleic acid and linolenic acid or a glyceride ester thereof from unsaturated acid source 32 at unsaturated acid treatment station 33 (the range of weight ratios of treating unsaturated acid:rinsed clothes on a dry basis being between 0.05% up to 0.7%). The resulting acid treated-rinsed clothes are then exposed at treatment station 36 to air, oxygen or ozone at a pressure of about 1 up to about 100 atmospheres pressure and prior to, simultaneously with or subsequent to said air, oxygen or ozone treatment is carried out using ultraviolet light rays from ultraviolet light source 35 for a period of from about 0.5 minutes up to about 20 minutes. The thus-treated clothing is then treated with a composition of aldehydes from aldehyde source 37 at aldehyde treatment station 38, the composition being:

(a) from about 0.5 up to about 5% by weight of said composition of n-hexanal;
(b) from about 2 up to about 12% by weight of said composition of n-heptanal;
(c) from about 5 up to about 15% by weight of said composition of n-octanal;
(d) from about 40 up to about 70% by weight of said composition of n-nonanal;

(e) from about 10 up to about 30% by weight of said composition of n-decanal;

(f) from about 0.5 up to about 5% by weight of said composition of n-undecanal;

(g) from about 0.5 up to about 5% by weight of said composition of n-dodecanal;

(h) from about 0.5 up to about 5% by weight of said composition of n-tridecanal;

(i) from about 0 up to about 5% by weight of said composition of n-tetradecanal;

(j) from about 0 up to about 5% by weight of said composition of n-pentadecanal.

The thus-treated clothing is then dried using an aromatic clothes drier on a standard 40 minute drying cycle and the resulting dried clothing has a pleasant fresh air dried, natural-light exposed aroma at testing station 30.

In determining the head space volatiles above various types of cloth using the apparatus illustrated in FIGS. 4(A) and 4(B), cloth (nylon, cotton or polyester); and filter paper controls in the alternative, 44 are placed in cylinder 40, maintained using cooling water in jacket 48 (entering at 49A and leaving at 49B). Nitrogen from nitrogen source 41 is passed through manifold 42 into the cylinder 40 at location 43 and through cloth 44 into the head space 45. The gas then passes through a Tenax-GC® trap 46 into the surrounding atmosphere 47. The Tenax-GC® trap traps the head space volatiles which are subsequently analyzed using GLC apparatus. Tenax-GC® is a porous polymer which is actually a 2,6-diphenyl-polyphenylene oxide polymer produced by the AKZO Research Laboratories of Delft, Netherlands.

FIG. 5 is the GLC profile for the volatiles in the head space above air dried cotton cloth as more particularly described in Example I(A). The peak indicated by reference numeral "50" is the peak for n-hexanal. The peak indicated by reference numeral "51" is the peak for n-heptanal. The peak indicated by reference numeral "52" is for n-octanal. The peak indicated by reference numeral "53" is for n-nonanal. The peak indicated by reference numeral "54" is for n-decanal. The peak indicated by reference numeral "55" is for n-undecanal. The peak indicated by reference numeral "56" is for n-dodecanal. The peak indicated by reference numeral "57" is for n-tridecanal. The peak indicated by reference numeral "58" is for n-tetradecanal. The peak indicated by reference numeral "59" is for n-pentadecanal.

The quantities of the foregoing n-alkanals in the head space are as follows:

| | |
|---|---|
| n-hexanal | 0.6% |
| n-heptanal | 8.5% |
| n-octanal | 10.0% |
| n-nonanal | 40.0% |
| n-decanal | 12.0% |
| n-undecanal | 3.0% |
| n-dodecanal | 2.0% |
| n-tridecanal | 1.0% |
| n-tetradecanal | 0.5% |
| n-pentadecanal | 0.3% |

The volatiles in the head space also include minor trace quantities of toluene, isomers of xylene, ethyl benzene and $C_9$–$C_{14}$ alkanes.

The conditions for the foregoing GLC analysis are: 400'×0.32" SE-30 column programmed at 70°–200° C. at 2° and 4° C. per minute.

FIG. 6 is the GLC profile for a similar head space analysis as more specifically described in Example I(B).

In carrying out Example I(B) using the apparatus depicted in FIGS. 4(A) and 4(B), the GLC profile contains the following peaks as indicated by the following reference numerals:

| Reference Numeral | Contents of Peak |
|---|---|
| "60" | n-hexanal |
| "61" | n-heptanal |
| "62" | n-octanal |
| "63" | n-nonanal |
| "64" | n-decanal |
| "65" | n-undecanal |
| "66" | n-dodecanal |
| "67" | n-tridecanal |
| "68" | n-tetradecanal |

The conditions for this GLC analysis are the same as for the one depicted by FIG. 5, namely: 400'×0.32" SE-30 column programmed at 70°–200° C. at 2° and 4° C. per minute.

FIG. 7 is the GLC profile for the volatiles in the head space above fresh air dried filter paper previously impregnated with cottonseed oil as more specifically described in Example II. The cottonseed oil is first impregnated into the filter paper and the resultant impregnated filter paper is air dried in sunlight. The resulting air dried filter paper has a lactonic (peachy) aldehydic-like aroma profile.

The following reference numerals on FIG. 7 are for the following compounds:

| Reference Numeral | Compound | Percentage of Compound in Head Space |
|---|---|---|
| "70" | n-pentanal | 4.4% |
| "71" | n-hexanal | 48.6% |
| "72" | n-heptanal | 0.2% |
| "73" | 2-hexenal | 3.0% |
| "74" | 2-heptenal | 0.3% |
| "75" | 2-pentylfuran | 2.4% |
| "76" | 3-octen-2-one | 4.0% |
| "77" | 2-octenal | 16.0% |
| "78" | n-nonanal | 7.0% |
| "79" | 2-nonenal | 2.9% |
| "701" | 2-decenal | 0.5% |

In contrast to the fresh air dried sunlight exposed filter paper impregnated with cottonseed oil, the same filter paper was dried in an automatic clothes drier after being impregnated with cottonseed oil and the resulting aroma was "fatty, very oily, woody".

FIG. 8 is the GLC profile for the head space above the filter paper previously impregnated with cottonseed oil and then dried in the automatic clothes drier. The peak indicated by reference numeral "80" is the peak for n-pentanal and the peak indicated by reference numeral "81" is the peak for n-hexanal. The GLC conditions for FIG. 7 are the same as for FIG. 8; a 400'×0.32" SE-30 column programmed at 70°–200° C. at 2° and 4° C. per minute. The apparatus used is the apparatus depicted in FIGS. 4(A) and 4(B).

FIGS. 9, 10 and 11 are GLC profiles for head space volatiles above, respectively, non-impregnated filter paper; untreated polyester and untreated nylon, each of which is tested in the apparatus of FIGS. 4(A) and 4(B). In each case the GLC conditions were: 400'×0.32" SE-30 column programmed at 70°–200° C. at 2° and 4° C. per minute. Each of the tests is more fully described herein in Examples III(A), III(B) and III(C), infra. Each of the samples, the filter paper, the polyester and the nylon was dried in fresh air in the presence of natural sunlight. The ambient air was sampled and the GLC profile of the ambient air is set forth in FIG. 12.

As to the filter paper which was air dried in natural sunlight, no discernible or appreciable aroma emanated from said filter paper.

As to the polyester, the GLC for which is in FIG. 10, the peak indicated by reference numeral "100" is for benzene. The peak indicated by reference numeral "101" is for n-hexanal. The peak indicated by reference numeral "102" is for ethyl benzene. The peak indicated by reference numeral "103" is for n-heptanal. The peak indicated by reference numeral "104" is for benzaldehyde. The peak indicated by reference numerals "105A" and "105B" is for isomers of xylene. The peak indicated by reference numeral "106" is for n-nonanal. The peak indicated by reference numeral "107" is for naphthalene. The peak indicated by reference numeral "108" is for 1-methylnaphthalene. The peak indicated by reference numeral "109" is for silicon. In general, the aroma of the natural air dried polyester is described as "dusty, new clothing-like".

Referring to FIG. 11, the GLC profile for the volatiles in the head space above nylon cloth that was previously air dried in the presence of natural sunlight, the following reference numerals pertain to the following compounds:

| Reference Numeral | Compound |
|---|---|
| "110" | n-heptanal |
| "111" | n-nonane |
| "112" | benzaldehyde |
| "113" | n-octanal |
| "114" | n-decane |
| "115" | n-nonanal |
| "116" | n-undecane |
| "117" | silicon |
| "118" | n-decanal |
| "119" | n-undecanal |
| "1101" | silicon |
| "1102" | n-dodecanal |

In general, the overall aroma of the natural air dried nylon is "slightly dusty, fatty and aldehydic".

A sample of the air which was used to air dry the filter paper, untreated polyester and untreated nylon as more particularly described in Examples III(A), III(B) and III(C) was taken using an air sampling apparatus named: "Nutech 221 AC/DC Gas sampler" manufactured by the Nutech Corporation of Durham, N.C. A GLC profile was taken for the air sample, first unconcentrated (FIG. 12; reference numeral "130") and then concentrated onto a Tenax-GC® polymer (a porous polymer manufactured by AKZO Research Laboratories of Delft, Netherlands consisting essentially of a 2,6-diphenyl-polyphenylene oxide polymer). Thus, the profile indicated by reference numeral "130" is the original GLC profile (conditions: 400′×0.32″ SE-30 column programmed at 70°-200° C. at 2° and 4° C. per minute) and the profile indicated by reference numeral "140" is the transferred concentrate of the peaks of GLC profile 130 onto Tenax-GC® polymer. Thus, on the GLC profile indicated by reference numeral "140", the following reference numerals are for the following substances:

| Reference Numeral | Substance |
|---|---|
| "120" | air |

-continued

| Reference Numeral | Substance |
|---|---|
| "121" | n-octane |
| "122" | toluene |
| "123" | xylene isomer |
| "124" | xylene isomer |
| "125" | benzaldehyde |
| "126A" and "126B" | isomers of xylene |
| "127" | n-undecane |
| "128" | naphthalene |
| "129" | silicon |
| "1201" | n-tridecane |
| "1202" | silicon |
| "1203" | silicon |
| "1204" | n-nonane |
| "1205" | n-decane |
| "1206" | n-dodecane |
| "1207" | n-undecane |

A composition of straight chain unsaturated aldehydes defined as a composition of matter consisting essentially of:

(a) from about 0.5 up to about 5% by weight of said aldehyde composition of n-hexanal;
(b) from about 2 up to about 12% by weight of said aldehyde composition of n-heptanal;
(c) from about 5 up to about 15% by weight of said aldehyde composition of n-octanal;
(d) from about 40 up to about 70% by weight of said aldehyde composition of n-nonanal;
(e) from about 10 up to about 30% by weight of said aldehyde composition of n-decanal;
(f) from about 0.5 up to about 5% by weight of said aldehyde composition of n-undecanal;
(g) from about 0.5 up to about 5% by weight of said aldehyde composition of n-dodecanal;
(h) from about 0.5 up to about 5% by weight of said aldehyde composition of n-tridecanal;
(i) from about 0 up to about 5% by weight of said aldehyde composition of n-tetradecanal;
(j) from about 0 up to about 5% by weight of said aldehyde composition of n-pentadecanal;

are useful as olfactory agents. Hereinafter, this mixture of aldehydes will be termed "mixture of straight chain aldehydes of our invention". The said mixture of straight chain aldehydes of our invention can be incorporated into a wide variety of compositions each of which will be enhanced or augmented by their fresh air and sunlight dried cloth, fresh linen-like nuances.

The mixture of straight chain aldehydes of our invention can be added to perfume compositions as such or can be added to mixtures of materials in fragrance imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the mixture of straight chain aldehydes of our invention are useful as olfactory agent(s) and fragrance(s).

The term "perfume composition" is used herein to mean a mixture of compounds including, for example, natural essential oils, synthetic essential oils, alcohols, aldehydes (other than the mixture of straight chain aldehydes of our invention) ketones, esters, lactones, nitriles and frequently hydrocarbons which are admixed so that the combined odors of the individual components produce a pleasant or desired fragrance. Such perfume compositions usually contain (a) the main note or "bouquet" or foundation stone of the composition, (b) modifiers which round off and accompany the main note, (c) fixatives which include odorous substances which lend a particular note to the perfume throughout all stages of evaporation and substances which retard evaporation and (d) topnotes which are usually low-boiling, fresh-smelling materials. Such perfume compositions of our invention can be used in conjunction with carriers, vehicles, solvents, dispersants, emulsifiers, surface active agents, aerosol propellants and the like.

In perfume compositions, the olfactory components contribute their particular olfactory characteristics but the overall effect of the perfume composition will be the sum of the effect of each ingredient. Thus, the mixture of straight chain aldehydes of our invention can be used to alter, augment, modify or enhance the aroma characteristics of a perfume composition or a perfumed article, for example, by highlighting or moderating the olfactory reaction contributed by another ingredient of the composition.

The amount of the mixture of straight chain aldehydes of our invention which will be effective in perfume compositions depends upon many factors including the other ingredients, the amounts and the effects which are desired. It has been found that perfume compositions containing as much as 100% or as little as 0.05% by weight of the mixture of straight chain aldehydes of our invention, or even less, can be used to impart a powerful, long-lasting, stable air and sunlight dried cloth, fresh, linen-like aroma to soaps, cosmetics, fragranced polymers, detergents, fabric softeners and other products. The amount employed will depend upon considerations of cost, nature of the end product, the effect desired in the finished product and particular fragrance sought.

The mixture of straight chain aldehydes of our invention as disclosed herein can be used as such in a fragrance modifying composition or in a perfume composition as an olfactory component in detergents (e.g. anionic, cationic, nonionic or zwitterionic solid or liquid detergent) and soaps, space odorants and deodorants; perfumed plastics (e.g. polyethylene and polypropylene); perfume compositions; colognes, bath preparations such as bath oils, bath salts; hair preparations such as lacquers, brilliantines, pomades and shampoos; fabric softener compositions, fabric softener articles such as Bounce® (manufactured by the Procter & Gamble Company of Cincinnati, Ohio), cosmetic preparations such as creams, powders, deodorants, hand lotions, sun screens; powders such as talcs, dusting powders, face powders and the like. When the mixture of straight chain aldehydes of our invention are used in perfumed articles such as the foregoing, such mixture of straight chain aldehydes of our invention can be used in amounts of 0.01% or lower and generally it is preferred not to use more than 5% in the finished perfumed articles since the use of too much will tend to unbalance the total aroma and will needlessly raise the cost of the article. Thus, in summary, in perfumed articles, the mixture of straight chain aldehydes of our invention may be used in the range of from about 0.01% up to about 5.0%.

In addition, the perfume composition or fragrance composition of our invention can contain a vehicle or carrier for the mixture of straight chain aldehydes of our invention. The vehicle can be a liquid such as a non-toxic alcohol (e.g. 95% food grade ethanol), a non-toxic glycol (e.g. 1,2-propylene glycol) or the like. The carrier can also be an absorbent solid such as a gum (e.g. gum arabic, guar gum or xanthan gum) or components for encapsulating the composition (such as gelatin as by coacervation; or such as a urea-formaldehyde prepolymer as by means of polymerization of a shell around a liquid perfume center).

Furthermore, the perfume composition or fragrance composition of our invention can be incorporated into thermoplastic or thermoset resins. Thus, for example, the composition of our invention can be incorporated (as further exemplified infra) into polyolefins to form a scented polyolefin as more specifically set forth in U.S. Pat. No. 3,505,432 issued on Apr. 7, 1970 (the specification for which is incorporated by reference herein) or U.S. Pat. No. 4,247,498 issued on Jan. 27, 1981 (the specification for which is incorporated by reference herein). Furthermore, the mixtures of straight chain aldehydes of our invention may be incorporated in polymers as more specifically set forth in the patents listed below, the specifications for which are incorporated by reference herein:

| U.S. Pat. No. | Title |
|---|---|
| 3,091,567 | "Encapsulating Agents with Controlled Water Repellency" |
| 3,400,890 | "Fragrance Releasing Device" |
| 3,576,760 | "Water Soluble Entrapping" |
| 3,596,833 | "Fragrance-Releasing Flower-pot" |
| 3,780,003 | "Polymers of Alkoxy and Hydroxy Alkyl Acrylates or Methacrylates" |
| 3,670,073 | "Hydrophilic Polymer Containing Aerosol" |
| 3,681,248 | "Water Soluble Entrapping of a Fragrance" |
| 4,226,944 | "Process for a Polyurethane Foam Containing Fragrance" |
| 4,286,754 | "Controlled-Rate Liquid Dispenser" |
| 3,220,960 | "Cross-Linked Hydrophilic Polymers and Articles Made Therefrom" |
| 3,325,453 | "Polymerization Method Wherein the Rate of Initiator Addition is Dependent on the Reaction Temperature" |
| 3,574,822 | "Powdered Cosmetics of Hydrophilic Hydroxy Lower Alkyl Acrylates and Methocrylates" |
| 3,574,826 | "Hydrophilic Polymers having Vitamins Absorbed Therein" |
| 3,577,512 | "Sustained Release Tablets" |
| 3,577,518 | "Hydrophilic Hair Spray and Hair Setting Preparations" |
| 3,641,237 | "Zero Order Release Constant Elution Rate Drug Dosage" |
| 3,660,071 | "Water Soluble Entrapping of a Pesticide" |
| 3,660,563 | "Water Soluble Entrapping of a Drug" |
| 3,728,314 | "Chemical Composition for Viscosity Control and Film" |
| 3,728,317 | "Optical Contact Lenses and Related Devices" |
| 3,731,993 | "Lens Material for Reducing Effective Color Vision" |
| 3,854,982 | "Method for Preparing Hydrophilic Polymer Grafts Including Irradiation" |
| 3,876,768 | "Sterilization of Soft, Hydrophilic Acrylate and Methacrylate Copolymer Materials" |
| 3,877,431 | "Ostomy Gasket" |
| 3,896,753 | "Hydrophilic Polymer Coating for Underwater Structures" |
| 3,927,203 | "Cosmetic Compositions Employing Certain Co-polymers" |
| 3,933,407 | "Articles Coated with Synergistic Anti-Fog Coatings Based on Hydrophilic Polymers and Organosiloxane Oxyalkylene Block Copolymers" |
| 3,959,237 | "Sustained Release Polymers" |
| 4,267,281 | "Controlled Release Pesticides" |

-continued

| U.S. Pat. No. | Title |
|---|---|
| 4,292,301 | "Polymeric Diffusion Matrix Containing Ephedrine" |
| 4,295,987 | "Cross-Linked Sodium Polyacrylate Absorbent" |
| 4,297,220 | "Macroreticulated Copolymer Absorption Process" |

Referring to FIGS. 13 and 14 in particular, the apparatus used in producing polymeric fragrances comprises a device for forming a scented polyolefin (for example) pellets which comprises a vat or container 210 into which a mixture of polyolefins such as polyethylene and an aromatic substance or scented material is placed (in this case, the mixture of aldehydes of our invention). The container is closed by an air tight lid 228, clamped to the container by bolts 265. A stirrer 273 traverses the lid or cover 228 in air tight manner and is rotated in a suitable manner. A surrounding cylinder 212 having heated coils which are supplied with electric current through cable 224 from a rheostat or control 216 is operated to maintain the temperature inside the container 210 such that polyethylene or other thermoplastic polymer in the container will be maintained in the molten or liquid state. It has been found advantageous to employ a colorless, odorless polymer (e.g. polyethylene) with a viscosity ranging between 180 and 220 Saybolt seconds and having a melting point in the range of 200°-280° F. The heater 220 is operated to maintain the upper portion of the container 210 within a temperature range of from 250°-350° F. The bottom portion of the container 218 is heated by means of heating coils 222 heated through a control 220 connected thereto through a connecting wire 226 to maintain the lower portion of the container 218 within a temperature range of from 250°-350° F.

Thus, polymer (e.g. polyolefin) added to the container 210 is heated from 10-12 hours whereafter a scent or aroma imparting material (the mixture of aldehydes to create the fresh air aroma) is quickly added to the melt. The material must be compatible with polyolefin and forms a homogeneous liquid melt therewith. The scented material is of a type for the particular aroma desired and formulated specifically for the scenting purpose for which the polyolefin will be employed. The heat resisting coils and aromatic materials in some instance in solid or powdered form may be employed and added to the polyolefin in the container 210. Generally about 10-30% by weight of scenting material are added to the polyolefin.

After the scent imparting material is added to the container 210, the mixture is stirred for a few minutes, for example 5-15 minutes, and maintained within the temperature ranges indicated previously by the heating coils 212 and 218, respectively. The controls 216 and 220 are connected through cables 224 and 226 to a suitable supply of electric current for supplying the power for heating purposes.

Thereafter, the valve "V" is opened permitting the mass to flow outward through conduit 232 having a multiplicity of orifices 234 adjacent to the lower side thereof. The outer end of the conduit 232 is closed so that the liquid polymer (e.g. polyolefin) and aroma mixture will continuously drop through the orifices 234 downwardly from the conduit 232. During this time, the temperature of the polymer (e.g. polyolefin) and aroma mixture in the container 210 is accurately controlled so that a temperature in the range of from about 210°-275° F. will exit in the conduit 232. The regulation of the temperature through the control 216 and the control 220 is essential in order to insure temperature balance to provide for the continuous dropping or dripping of molten polymer (e.g. polyolefin) and scenting (that is mixture of aldehydes) mixture through the orifices 234 at a range which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 259 which is advantageously filled with water or some other suitable cooling liquid to insure the rapid cooling of each of the pellets. The pellets 244 are then collected from the container 259 and utilized in a process as illustrated infra.

A feature of this aspect of the process of our invention is the provision for moistening the conveyor belt 238 to insure rapid formation of the solid polymer (e.g. polyolefin) scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 259 which is continuously fed with water 252 to maintain a level 254 for moistening a sponge element 256 which bears against the exterior surface of the belt 238.

The following examples are illustrative and the invention is to be considered to be restricted thereto only as indicated in the appended claims. All parts and percentages given herein are by weight unless otherwise specified.

EXAMPLE I(A)

Cotton bath towels (700 grams) are washed in 40 grams of unscented Fab ® detergent and then air dried in the presence of sunlight for a period of 8 hours. The bath towels are then purged in a slow stream of nitrogen (30 ml per minute) for a period of 24 hours. The effluent is collected in a Tenax-GC ® trap in the apparatus of FIG. 4(A). The trap is then analyzed by GCMS (conditions: 400'×0.32" SE-30 column programmed at 70°-200° C. at 2° and 4° C. per minute) and the following compounds and percentages are identified as set forth in FIG. 5:

| Reference Numeral on FIG. 5 | Component | Percentage |
|---|---|---|
| "50" | n-hexanal | 0.6% |
| "51" | n-heptanal | 8.5% |
| "52" | n-octanal | 10.0% |
| "53" | n-nonanal | 40.0% |
| "54" | decanal | 12.0% |
| "55" | undecanal | 3.0% |
| "56" | dodecanal | 2.0% |
| "57" | tridecanal | 1.0% |
| "58" | tetradecanal | 0.5% |
| "59" | pentadecanal | 0.3% |

EXAMPLE I(B)

Three 700 gram bath towels are washed three times in hot water without the use of any laundry detergent in a washing machine. The cloth is then air dried in sunlight for a period of seven hours. The dried cloth is then placed into the head space measuring apparatus of FIGS. 4(A) and 4(B) and the apparatus is operated using 30 ml nitrogen per minute for a period of 48 hours. The volatiles in the head space are absorbed on the Tenax-GC® resin and then analyzed by GC/MS (conditions: 400'×0.32" SE-30 column programmed at 70°-200° C. at 2° and 4° C. per minute). The GLC profile is set forth in FIG. 6. The following components are identified as being the following peaks on the GLC profile of FIG. 6:

| Reference Numeral | Constituent | Percentage |
|---|---|---|
| "60" | n-hexanal | 0.64% |
| "61" | n-heptanal | 8.30% |
| "62" | n-octanal | 10.00% |
| "63" | n-nonanal | 40.00% |
| "64" | n-decanal | 11.30% |
| "65" | n-undecanal | 2.70% |
| "66" | n-dodecanal | 1.60% |
| "67" | n-tridecanal | 1.20% |
| "68" | n-tetradecanal | 0.43% |
| "69" | n-pentadecanal | 0.20% |

EXAMPLE I(C)

Water washed electric dried cotton cloth shows no formation of cloth odor constituents. This material is then re-washed and air dried in natural sunlight for a period of 72 hours and then purged for a period of 48 hours onto a Tenax-GC® trap using the apparatus of FIGS. 4(A) and 4(B) according to the procedure of Example I(B).

GLC analysis (conditions: 400'×0.32" SE-30 column programmed at 70°-200° C. at 2° and 4° C. per minute) yields the following results:

| Component | Percentage |
|---|---|
| n-hexanal | 1.30% |
| n-heptanal | 4.40% |
| n-octanal | 10.80% |
| n-nonanal | 44.00% |
| unknown (aldehyde) | 6.00% |
| n-decanal | 19.60% |
| n-undecanal | 1.60% |
| n-dodecanal | 0.61% |
| n-tridecanal | 0.57% |

EXAMPLE I(D)

Three cotton towels are washed in an electric washing machine and dried for one hour in an electric drier. These towels weighing about 700 grams each are then placed in the head space purge apparatus of FIGS. 4(A) and 4(B) and purged in a slow stream of nitrogen (30 ml per minute) for a period of 48 hours. The head space is analyzed and the only compound identified is ionol.

EXAMPLE II

Five 2' diameter coarse filter paper discs are impregnated with cottonseed oil (12.5% by weight cottonseed based on the dry weight of the filter paper). The discs are then wet with water and air dried for 16 hours in fresh air and sunlight. The resulting discs are placed in the purging chamber of FIGS. 4(A) and 4(B) and purged for a period of 48 hours at 45° C. with nitrogen at 30 ml per minute. The GLC profile for the trapped volatiles in the Tenax-GC® polymer is set forth in FIG. 7. The resulting volatiles have a lactonic (peachy) aldehydic aroma which is aesthetically pleasing. The following reference numerals refer to the following compounds and their percentages in FIG. 7:

| Reference Numeral | Compound | Percentage |
|---|---|---|
| "70" | n-pentanal | 4.4% |
| "71" | n-hexanal | 48.6% |
| "72" | n-heptanal | 0.2% |
| "73" | 2-hexenal | 3.0% |
| "74" | 2-heptenal | 0.3% |
| "75" | 2-pentyl-furan | 2.4% |
| "76" | 3-octen-2-one | 4.0% |
| "77" | 2-octenal | 16.0% |
| "78" | n-nonanal | 7.0% |
| "79" | 2-nonenal | 2.9% |
| "701" | 2-decenal | 0.5% |

When, instead of air drying the resulting cottonseed oil-impregnated filter papers, the same experiment is carried out using an electric drier, the GLC profile of the head space volatiles is as is set forth in FIG. 8 and the head space volatiles have a "fatty, very oily, woody" aroma. Reference numeral "80" on FIG. 8 is for n-pentanal and reference numeral "81" is for n-hexanal.

EXAMPLE III

Untreated filter paper, untreated polyester cloth and untreated nylon are wet with water and air dried as is set forth in Examples III(A), III(B) and III(C) infra. The air drying in fresh air in the presence of natural sunlight.

The air is sampled using a NuTech No. 221 AC/DC gas sampler manufactured by the NuTech Corporation of Durham, N.C. and FIG. 12 is the GLC profile for the said air sample. The GLC profile indicated by reference numeral "130" in FIG. 12 is the original GLC prior to concentration on a Tenax-GC® polymer. The GLC profile represented by reference numeral "140" is the GLC profile of the concentrate on Tenax-GC® polymer transferred from the GLC profile indicated by reference numeral "130".

The constituents of the air are set forth on the GLC profile indicated by reference numeral "140" in FIG. 12 and are as follows:

| Reference Numeral | Constituent |
|---|---|
| "120" | air |
| "121" | n-octane |
| "122" | toluene |
| "123" | xylene isomer |
| "124" | xylene isomer |
| "125" | benzaldehyde |
| "126A" and "126B" | xylene isomers |
| "127" | n-undecane |
| "128" | naphthalene |
| "129" | silicon |
| "1201" | n-tridecane |
| "1202" | silicon |
| "1203" | silicon |
| "1204" | n-nonane |
| "1205" | n-decane |
| "1206" | n-dodecane |
| "1207" | n-undecane |

EXAMPLE III(A)

Five 2' diameter coarse filter paper discs are set with water and air dried for 16 hours in fresh air and natural sunlight. The odor evaluation is: "no odor is perceived". The resulting material is placed in the purging chamber of the apparatus depicted in FIGS. 4(A) and 4(B) and purged for 48 hours at 45° C. at 30 ml per minute with nitrogen. Analysis via GLC and MS indicates no real constituents in the spectra. The GLC profile is set forth in FIG. 9.

EXAMPLE III(B)

Polyester cloth (Dacron®) having a weight of 700 grams is water washed and air dried in fresh air and sunlight for a period of eight hours. The resulting material is purged in the apparatus depicted in FIGS. 4(A) and 4(B) using nitrogen at a rate of 30 ml per minute for a period of 48 hours at a temperature of 45° C. The purging gas is passed through the Tenax-GC® in a trap. The head space is analyzed by means of GLC analysis (conditions: 400'×0.32" SE-30 column programmed at 70°-200° C. at 2° and 4° C. per minute). The GLC profile is set forth in FIG. 10. The constituents of the volatiles in the head space collected in the Tenax-GC® trap of the apparatus depicted in FIGS. 4(A) and 4(B) is as follows:

| Reference Numeral on GLC Profile | Constituent |
|---|---|
| "100" | benzene |
| "101" | n-hexanal |
| "102" | ethyl benzene |
| "103" | n-heptanal |
| "104" | benzaldehyde |
| "105" | xylene isomers |
| "106" | n-nonanal |
| "107" | naphthalene |
| "108" | 1-methyl naphthalene |
| "109" | silicon |

The head space volatiles have an aroma that can be described as "dusty, new clothing-like".

EXAMPLE III(C)

Nylon cloth (700 grams) is washed in fresh water and air dried in fresh air and natural sunlight for a period of 8 hours. The resulting material is then placed in the apparatus depicted in FIGS. 4(A) and 4(B) and purged for a period of 48 hours at 45° C. with nitrogen at 30 ml per minute. The head space volatiles are trapped in a Tenax-GC® column and the trap is analyzed by means of GLC analysis and the GLC profile is set forth in FIG. 11. The constituents of the head space volatile composition and a number of percentages are set forth in the table below:

| Reference Numeral on GLC Profile | Constituent | Percentage |
|---|---|---|
| "110" | n-heptanal | 9.7% |
| "111" | n-nonane | — |
| "112" | benzaldehyde | — |
| "113" | n-octanal | 11.0% |
| "114" | n-decane | — |
| "115" | n-nonanal | 38.0% |
| "116" | n-undecane | — |
| "117" | silicon | — |
| "118" | n-decanal | 1.0% |
| "119" | n-undecanal | — |
| "1101" | silicon | — |
| "1102" | n-dodecanal | — |

The aroma of the dried nylon cloth is described as "slightly dusty, fatty, aldehydic".

EXAMPLE IV(A)

Preparation of Fresh Air Aroma Composition

The following mixture is prepared:

| Ingredients | Grams |
|---|---|
| n-hexanal | 0.1 |
| n-heptanal | 0.6 |
| n-octanal | 1.0 |
| n-nonanal | 3.0 |
| n-decanal | 1.3 |
| n-undecanal | 0.1 |
| n-dodecanal | 0.1 |
| n-tridecanal | 0.1 |
| n-tetradecanal | 0.1 |

The resulting mixture has a rosey, aldehydic, fresh, ozone-like aroma.

EXAMPLE IV(B)

The mixture of Example IV(A) (1 gram) is added to 99 grams of ethyl alcohol. One gram of the resulting ethyl alcohol solution is mixed with 49 grams of ethyl alcohol to yield a 0.05% solution. 65 ml of freon is added to the resulting mixture to form an "aerosol spray". The aerosol spray, when used, has a "fresh air odor".

EXAMPLE V

Six cotton bath towels (700 grams each) are washed in hot water using no detergent. The resulting cloth is then air dried for a period of 8 hours. Half of the towels (3 in number) are placed in an electric drier for one hour. The other half of the towels are air dried using fresh air and natural sunlight. Both sets of towels are evaluated:

A. The fresh air dried towels exposed to natural sunlight have a fresh air odor which can be described as "aldehydic, hot ironing board aroma, fresh linen-like".

B. The electric drier-dried towels have a weak, nondescript, aesthetically displeasing aroma.

Both sets of towels are then placed into the head space apparatus of FIGS. 4(A) and 4(B) and purged for 48 hours with nitrogen at 45° C. at 30 ml nitrogen per minute. GLC analysis indicates that the fresh air dried cotton cloth head space contains $C_6$-$C_{10}$ aldehydes. The cloth dried in the electric drier has no aldehydes. The cloth air dried followed by drying using an electrical drier contain no such aldehydes (but a small amount of cumene is detected).

EXAMPLE VI

Rose Formulation

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenyl ethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |

-continued

| Ingredients | Parts by Weight |
|---|---|
| Phenyl ethyl acetate | 20.0 |
| Rose oxide | 8.0 |
| Guaiacol | 30.0 |
| 1-citronellal | 90.0 |
| Neryl acetate | 3.0 |
| Clove bud oil | 1.0 |
| Cadinene | 2.0 |
| Guaiene | 1.0 |
| Gum terpentine | 12.0 |
| Alpha-pinene | 1.0 |
| Myrcene | 5.0 |
| Limonene | 2.0 |
| p-cymene | 1.0 |
| [ 3-methyl-1-phenyl-pentanol-5 (0.1% solution in diethyl phthalate) ] | 30.0 |
| Beta damascenone (0.01% in diethyl phthalate) | 15.0 |

To the foregoing formulation, 15 parts by weight of the aldehyde composition of Example IV(A) is added. The resulting mixture has a much brighter, fresh air topnote and is more "rosey" on dry-out as compared to the same mixture without the aldehyde composition.

EXAMPLE VII

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| Mixture of aldehydes prepared according to Example IV (A) | A "fresh air", freshly dried linen aroma which is long lasting and intensive and aesthetically pleasing. |
| Perfume composition of Example VI | A rich, rosey, fruity aroma with fresh air and linen topnotes. |

EXAMPLE VIII

Perfumed Liquid Detergents

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table I of Example VII are prepared containing 0.10%, 0.15%, 0.20%, 0.25%, 0.30% and 0.35% of the substance set forth in Table I of Example VII. They are prepared by adding and homogeneously mixing the appropriate quantity of substance set forth in Table I of Example VII in the liquid detergent. The detergents all possess excellent aromas as set forth in Table I of Example VII, the intensity increasing with greater concentrations of substance as set forth in Table I of Example VII.

EXAMPLE IX

Preparation of Colognes and Handkerchief Perfumes

Compositions as set forth in Table I of Example VII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example VII are imparted to the colognes and to the handkerchief perfumes at all levels indicated.

EXAMPLE X

Preparation of Soap Compositions

One hundred grams of soap chips (per sample) (Ivory ®, produced by the Procter & Gamble Company of Cincinnati, Ohio), are each mixed with one gram samples of substances as set forth in Table I of Example VII until homogeneous compositions are obtained. In each of the cases, the homogeneous compositions are heated under eight atmospheres pressure at 180° C. for a period of three hours and the resulting liquids are placed into soap molds. The resulting soap cakes, on cooling, manifest aromas as set forth in Table I of Example VII.

EXAMPLE XI

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| [ Neodol ® 45-11 (a $C_{14}$-$C_{15}$ alcohol ethoxylated with 11 moles of ethylene oxide ] | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example VII. Each of the detergent samples has an excellent aroma as indicated in Table I of Example VII.

EXAMPLE XII

Utilizing the procedure of Example I at column 15 of U.S. Pat. No. 3,632,396 (the disclosure of which is incorporated herein by reference), nonwoven cloth substrates useful as drier added fabric softening articles of manufacture are prepared wherein the substrate, the substrate coating, the outer coating and the perfuming material are as follows:

1. a water "dissolvable" paper ("Dissolvo Paper")
2. Adogen 448 (m.p. about 140° F.) as the substrate coating and
3. an outer coating having the following formulation (m.p. about 150° F.):
   57% $C_{20-22}$ HAPS
   22% isopropyl alcohol
   20% antistatic agent
   1% of one of the substances as set forth in Table I of Example VII.

Fabric softening compositions prepared according to Example I at column 15 of U.S. Pat. No. 3,632,396 having aroma characteristics as set forth in Table I of Example VII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example VII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener nonwoven fabrics and these aroma characteristics are described in Table I of Example VII, supra.

EXAMPLE XIII

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. Eight grams of the polymer are dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| [Dow Corning 473 fluid (prepared by the Dow Corning Corporation)] | 0.10 weight percent |
| [Tween 20 surfactant (prepared by ICI America Corporation)] | 0.03 weight percent |
| [One of the perfumery substances as set forth in Table I of Example VII, supra] | 0.10 weight percent |

The perfuming substances as set forth in Table I of Example VII add aroma characteristics as set forth in Table I of Example VII which are rather intense and aesthetically pleasing to the users of the soft-feel, good-hold pump hair sprays.

EXAMPLE XIV

Conditioning Shampoos

Monamid CMA (prepared by the Mona Industries Company) (3.0 weight percent) is melted with 2.0 weight percent) coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat® 775 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table I of Example VII is added to the mixture. The resulting mixture is cooled to 40° C. and blending is carried out for an additional one hour in each case. At the end of this blending period, the resulting material has a pleasant fragrance as indicated in Table I of Example VII.

EXAMPLE XV

Scented polyethylene pellets having a pronounced fresh air-dried linen aroma are prepared as follows:

Seventy-five pounds of polyethylene having a melting point of about 220° F. is heated to about 230° F. in a container of the kind illustrated in FIGS. 13 and 14. Twenty-five pounds of the aldehyde formulation of Example IV(A) is then quickly added to the liquified polyethylene, the lid 228 is put in place and the agitating means 273 are actuated. The temperature is maintained at about 225° F. and the mixing is continued for about 5–15 minutes. The valve "V" is then opened to allow flow of the molten polyethylene enriched with the aldehyde-containing material to exit through the orifices 234. The liquid falling through the orifices 234 solidifies almost instantaneously upon impact with the moving, cooled convey 238. Polyethylene beads or pellets 244 having a pronounced fresh air-dried linen scent are thus formed. Analysis demonstrates that the pellets contain about 25% of the aldehyde formulation so that almost no losses in the scenting substance did occur. These pellets may be called "master pellets".

Fifty pounds of the aldehyde-containing master pellets are then added to 1,000 pounds of unscented polyethylene powder and the mass is heated to the liquid state. The liquid is molded into thin sheets of films. The sheets of films have a pronounced fresh air-dried linen aroma.

EXAMPLE XVI

One hundred pounds of polypropylene are heated to about 300° F. Thirty pounds of the essence as described in Example IV(A) are added to tthe liquified polypropylene. The procedure is carried out in the apparatus shown in FIGS. 13 and 14. After mixing for about eight minutes, the valve "V" is opened to allow the exit of polypropylene scented material mixture whereby solid pellets having a pronounced perfume smell were formed on the conveyor (fresh air-dried linen aroma). The pellets thus obtained are then admixed with about twenty times their weight of unscented polypropylene and the mixture is heated and molded into flat discs. The flat discs have a strong and pleasant fresh air-dried, natural, light, dried linen smell and scent.

What is claimed is:

1. A process for augmenting or enhancing or imparting a fresh air aroma to a perfumed article selected from the group consisting of fabric softener compositions, fabric softener articles, cosmetic powders and hair shampoos comprising the step of adding to said perfumed article an aroma augmenting or enhancing quantity of an aldehyde composition consisting essentially of:

(a) from about 0.5 up to about 5% by weight of said aldehyde composition of n-hexanal;

(b) from about 2 up to about 12% by weight of said aldehyde composition of n-heptanal;

(c) from about 5 up to about 15% by weight of said aldehyde composition of n-octanal;

(d) from about 40 up to about 70% by weight of said aldehyde composition of n-nonanal;

(e) from about 10 up to about 30% by weight of said aldehyde composition of n-decanal;

(f) from about 0.5 up to about 5% by weight of said aldehyde composition of n-undecanal;

(g) from about 0.5 up to about 5% by weight of said aldehyde composition of n-dodecanal;

(h) from about 0.5 up to about 5% by weight of said aldehyde composition of n-tridecanal;

(i) from about 0 up to about 5% by weight of said aldehyde composition of n-tetradecanal;

(j) from about 0 up to about 5% by weight of said aldehyde composition of n-pentadecanal.

2. The process of claim 1 wherein the perfumed article is a fabric softener article.

3. The process of claim 1 wherein the perfumed article is a fabric softener composition.

4. The process of claim 1 wherein the perfumed article is a cosmetic powder.

5. The process of claim 1 wherein the perfumed article is a hair shampoo.

* * * * *